United States Patent
Sawan et al.

(10) Patent No.: US 7,519,429 B2
(45) Date of Patent: Apr. 14, 2009

(54) ELECTRONIC STIMULATOR IMPLANT

(76) Inventors: Mohammad Sawan, 597 Bord-de-l'Eau, Laval, Quebec (CA) H7X 1T9; Mostafa Elhilali, 2500 Pierre-Dupuy, Apt. 412, Montreal, Quebec (CA) H3C 4L1

( * ) Notice: Subject to any disclaimer, the term of this patent is extended or adjusted under 35 U.S.C. 154(b) by 0 days.

(21) Appl. No.: 10/151,315

(22) Filed: May 21, 2002

(65) Prior Publication Data
US 2002/0193840 A1    Dec. 19, 2002

Related U.S. Application Data

(63) Continuation-in-part of application No. 09/494,348, filed as application No. PCT/CA01/00074 on Jan. 31, 2001, now Pat. No. 6,393,323.

(51) Int. Cl.
*A61N 1/00* (2006.01)
*A61B 5/05* (2006.01)

(52) U.S. Cl. .............................. 607/60; 607/41; 607/62; 607/64; 607/118; 600/547

(58) Field of Classification Search ............. 607/40–41, 607/28, 547, 60, 62, 64, 188, 8; 600/547
See application file for complete search history.

(56) References Cited

U.S. PATENT DOCUMENTS

| | | | |
|---|---|---|---|
| 3,650,275 A * | 3/1972 | Von Der Mozel | ............. 607/76 |
| 3,662,758 A | 5/1972 | Glover | |
| 3,667,477 A | 6/1972 | Susset et al. | |
| 4,088,141 A * | 5/1978 | Niemi | ......................... 607/63 |
| 4,167,189 A | 9/1979 | Tachi et al. | |

(Continued)

FOREIGN PATENT DOCUMENTS

JP    10-108391    4/1998

(Continued)

OTHER PUBLICATIONS

A New Implantable System for Neural Selective Stimulation of the Bladder, S. Robin et al., IFESS 1997, pp. 1-4, Dept. of Electrical and Computer Engineering, École Polytechnique de Montréal and Dept. of Urology, McGill University, Montréal, Canada.

(Continued)

*Primary Examiner*—Mark W Bockelman
(74) *Attorney, Agent, or Firm*—Timothy J. Keefer; Polsinelli Shughart PC

(57) ABSTRACT

The present invention relates to lower urinary dysfunctions and more particularly to an electronic stimulator implant and method to improve bladder voiding and prevent bladder hyperreflexia. There is provided an electronic stimulator implant for which comprises a tonicity signal generator generating a tonicity signal which prevents bladder hyperreflexia combined with a voiding signal generator generating a voiding signal for voiding the bladder. The implant is connected to an end of an electrode, and the second end thereof is connected to a sacral nerve. When the voiding key (or switch) is activated, the voiding signal is generated which activates detrusor muscle contraction, causing bladder voiding. The voiding may be achieved without dyssynergia, by activating detrusor muscle contraction without activating external urethral sphincter contraction. The tonicity signal may be provided intermittently. The implant may be activated by a manually activated external controller.

4 Claims, 4 Drawing Sheets

U.S. PATENT DOCUMENTS

| | | | | |
|---|---|---|---|---|
| 4,607,639 | A | * | 8/1986 | Tanagho et al. ............... 607/40 |
| 4,688,575 | A | | 8/1987 | DuVall |
| 4,739,764 | A | | 4/1988 | Lue et al. |
| 4,771,779 | A | | 9/1988 | Tanagho et al. |
| 5,257,623 | A | | 11/1993 | Karasev et al. |
| 5,876,425 | A | | 3/1999 | Gord et al. |
| 5,941,906 | A | * | 8/1999 | Barreras et al. ............... 607/66 |
| 6,393,323 | B1 | * | 5/2002 | Sawan et al. .................. 607/41 |

FOREIGN PATENT DOCUMENTS

| | | |
|---|---|---|
| WO | WO 87 07511 | 12/1987 |
| WO | WO 96/20754 | 7/1996 |
| WO | WO 00/01320 | 1/2000 |

OTHER PUBLICATIONS

New Integrated Miniaturized Neuromuscular Stimulator to Enhance Bladder Voiding, S. Boyer et al., IFESS, 1999, pp. 1-4, Dept. of Electrical and Computer Engineering, Ecole Polytechnique de Montréal and Dept. of Urology, McGill University, Montréal, Canada.

A Miniaturized Implantable Bladder Selective Electrical Stimulator, M. Sawan et al, pp. 1-6, École Polytechnique de Montréal, 1998, Montréal, Canada.

Reduction of Bladder Outlet Resistance by Selective Sacral Root Stimulation Using High-Frequency Blockade In Dogs: An Acute Study, H.S. Shaker et al, vol. 160 pp. 901-907, Sep. 1998, Urology Research Laboratory, Royal Victoria Hospital, McGill University and the Dept. of Electrical Engineering, École Polytechnique, Montréal, Canada.

Selective Neural Stimulation to Improve Bladder Voiding: Chronic Experiments in Gods, S. Boyer et al., Dept. of Electrical and Computer Engineering, pp. 1-2, Dept. of Electrical and Computer Engineering, École Polytechnique de Montréal, and Dept. of Urology, McGill University, Montréal, Canada.

A Wireless Implantable Electrical Stimulator Based on Tow FPGAS, M. Sawan et al. ICEC 1996. École Polytechnique de Montréal, Dept. of Electrical and Computer Engineering, Montréal, Canada.

A Hand-Held Controller Dedicated to Implantable Stimulators, Simon Robin et al., Dept. of Electrical & Computer Engineering, Ecole Polytecyhnique de Montréal, Montréal, Canada pp. 5, FPD 1996.

Implantable Stimulation System Dedicated for Neural Selective Stimulation, S. Robin et al, Dept. of Electrical and Computer Engineering, École Polytechnique de Montréal, and Dept. of Urology, McGill University, Montréal, Canada, Med. Biol. Eng. Comput., 1998, pp. 36, 490-492.

Low-Power CMOS Implantable Nerve Signal Analog Processing Circuit, Adnan Harb et al., ICEC 1999. pp. 1-4, Ecole Polytechnique de Montréal, Dept. of Electrical and Computer Engineering, Montréal, Canada.

Implantable Measurement Technique Dedicated to the Monitoring of Electrode—Nerve Contact in Bladder Stimulators, C. Donfack et al., Medical & Biological Engineering & Computing 2000, vol. 38, pp. 465-468.

New Implantable Stimulator for Rehabilitation of the Bladder Functions, A, Ba, E.. Schneider et al., PolySTIM, Department of Electriccal Engineering, École Polytechnique de Montréal, Department of Urology, McGill University, Montreal, Canada, IFESS, Lujbljana, Slovenia, Jun. 2000.

New Stimulator Strategy to Improve the Bladder Function in Paraplegics: Chronic Experiments in Dogs, E. Schneider et al. PolySTIM, Department of Electriccal Engineering, École Polytechnique de Montréal, Department of Urology, McGill University, Montreal, Canada, EMBS, Turkey, Oct. 2001.

Selective Neurostimulation to Reduce the Hyperfolexia of the Detrusor and Avoid its Dyssenergia with the Sphincter, Mohamad Sawan, PolySTIM Neurotechnology Laboratory, Department of Electriccal Engineering, École Polytechnique de Montréal, Published in The International Society of Pelvic Neuromodulation, Phoenix, U.S.A., Jan. 2003.

* cited by examiner

ELECTRONIC STIMULATOR IMPLANT

CROSS REFERENCE TO RELATED APPLICATION

This application is a continuation of U.S. patent application Ser. No. 10/151,315 filed May 21, 2002 which is a continuation-in-part of U.S. patent application Ser. No. 09/494,348 filed Jan. 31, 2000, now U.S. Pat. No. 6,393,323 issued May 21, 2002, the subject matter of which is incorporated herewith by reference. This application also claims priority of International application No. PCT/CA01/00074, filed Jan. 31, 2001.

FIELD OF THE INVENTION

The present invention relates to lower urinary dysfunctions and to methods for improving same, and more particularly to an implantable electronic stimulator to prevent detrusor-sphincter dyssynergia and reduce detrusor hyperreflexia, in order to reduce the urgency and frequency of urination. The present invention further relates to a circuit for measuring an electrode-tissue contact impedance and responding thereto either by communicating the impedance value or state to an external implant controller or to adjust an amplitude of the implant's generated current.

BACKGROUND OF THE INVENTION

Normal urinary control and voiding are the result of complex interactions of smooth muscle, voluntary muscle, cerebral inhibition and the autonomic nervous system (ANS). These interactions are explained hereinafter with reference to FIG. 1.

The bladder B is a stretchable chamber defined by the pelvic floor muscle group, which includes a wall of smooth detrusor muscle M containing stretch receptors innervated with parasympathetic neurons P of autonomic nerve fibers A. The base of the bladder B, called the internal urethral sphincter I, is part of the detrusor muscle M and opens automatically when the bladder B contracts. A skeletal external urethral sphincter muscle E surrounds the urethra U at the bladder outlet and is innervated by somatic motor neurons S. As may be seen, the nerves that control the detrusor muscle also control the external urethral sphincter E. The somatic nerve fibers S and the autonomic nerve fibers A originate from sacral segments S2, S3 and S4 in a dorsal root D and a ventral root V. The dorsal root D transmits sensations from the bladder B to the spinal cord whereas the ventral root V transmits impulses from the spinal cord to the bladder B. The ventral root V is composed of somatic A-alpha fibers which innervate the external urethral sphincter E and of parasympathetic A-delta fibers which innervate the detrusor muscle M. The sympathetic system plays a role particularly in the area of the bladder neck and the proximal urethra during continence, increasing the bladder outlet resistance.

Urination or bladder voiding is a spinal reflex involving neurological control in the bladder wall or external urethral sphincter, in the autonomic center of the spinal cord and in the central nervous system (CNS) at the level of the Pontine Micturition Center (PMC) in the mid-brain, which is under the control of the cerebral cortex.

When the bladder is empty, the detrusor muscle is relaxed, the stretch receptors are quiescent and the external urethral sphincter is contracted and closed. The bladder becomes distended as it fills with urine from the kidneys and the stretch receptors are stimulated up to a threshold. The stretch receptors stimulate neurons to the sacral cord in a spinal reflex arc. The stretch receptors also stimulate the parasympathetic neurons through an ascending pathway to the PMC. The cerebral cortex through the PMC generates impulses through a descending pathway to suppress the spinal reflex arc.

Bladder voiding is voluntarily induced by interrupting the descending pathway from the cerebral cortex which inhibits the contraction of the external urethral sphincter, thereby acting together with the afferent pathway from the bladder stretch receptors to the cerebral cortex, resulting in external urethral sphincter relaxation, detrusor muscle contraction and initiating bladder voiding. Bladder voiding is delayed by activating the descending pathway from the cerebral cortex which inhibits contraction of the detrusor muscle and stimulates contraction of the external urethral sphincter, thereby overriding the ascending pathway from the bladder stretch receptors to the cerebral cortex.

A lower urinary dysfunction such as neurogenic bladder dysfunction manifests itself as partial or complete urinary retention, incontinence or frequent urination. Common problems associated therewith include urinary infections, urinary calculi, renal damage and "detrusor-sphincter dyssynergia", or simultaneous contraction of the detrusor muscle and the external urethral sphincter, which leads to increased bladder pressure, incontinence and ultimately kidney failure. Neurogenic bladder dysfunction may result (1) from congenital abnormalities such as myelomeningocele, filum terminale syndrome and other lesions of the spinal cord and cauda equina; (2) from diseases such as syphilis, diabetes mellitus, brain or spinal cord tumors, cerebrovascular accidents, ruptured intervertebral disk, and demyelinating or degenerative diseases such as multiple sclerosis and amyotrophic lateral sclerosis, or (3) from injuries of the brain, spinal cord or local nerve supply to the urinary bladder and its outlet, such as with transverse myelitis and transsection of the cord.

The most common acquired cause of severe neurogenic bladder dysfunction is spinal cord injury (SCI) or transsection resulting in paraplegia or quadriplegia. Paraplegic and quadriplegic patients exhibit involuntary control over their bladder and sphincter functions. In SCI patients, the brain cannot send messages below the level of injury, and messages from organs innervated by regions below the level of injury cannot reach the brain. Immediately after the SCI, the bladder becomes atonic, distended and, if neglected, exhibits continuous overflow dribbling during the "spinal shock" phase. Lesions to the lower spinal cord (sacral and lumbar segments) produce a flaccid paralysis of the bladder with overfilling thereof, while upper cord lesions (thoracic and cervical lesions) produce an automatic or spastic reflex bladder that empties spontaneously or as the result of somatic stimuli, with detrusor muscle hyperreflexia and detrusor-sphincter dyssynergia. Hyperreflexia consists of a hyperactivity of the ANS. It occurs when the overfull bladder sends impulses to the spinal cord, where they travel upward until they are blocked by the lesion at the level of injury. Since the impulses cannot reach the brain, the reflex arc stays activated, which increases activity of the sympathetic portion of the ANS and causes spasms.

Several treatment modalities are available to manage patients with neurogenic bladder dysfunction, such as indwelling (continuous) urethral catheter drainage or intermittent catheterization, to prevent overdistention of the detrusor muscle. However, the presence of the catheter in the male patient predisposes to urethritis, periurethritis, abscess formation and urethral fistula. Consequently, incision of the external urethral sphincter or sphincterotomy is often required to minimize outlet resistance and to maximize emptying of the bladder using condom drainage when the patient becomes incontinent.

Pharmacological management with medications producing an antispasmodic or anticholinergic effect on the bladder may alternatively be used to reduce spastic reflexes and involuntary contractions of the detrusor muscle, with some undesirable side effects.

Surgical procedures such as permanent urinary diversion may further be used to lower the risk of kidney damage. Upper tract diversion is accomplished by iteal or colon conduit. Permanent suprapubic cystostomy affords control in some patients only, and cutaneous vesicostomy with an external appliance may be used only in patients with no upper tract damage. Other surgical procedures such as ureterosigmoidostomy, cutaneous intubated ureterostomies and nephrostomies are not recommended, since most patients also lose rectal sphincter control, and indwelling catheters increase risks of stone formation and infection.

Devices such as artificial sphincters implanted around the urethra have also been used to control urinary continence in some patients.

Total functional recovery in any form of neurogenic bladder with the above-mentioned techniques remained uncommon.

Electrical stimulation of organs such as with pacemakers and cochlear implants was developed to restore organ functions impaired by a neurological disorder or an organ failure. Electrical stimulation may be used for pain relief, for maintaining or increasing a range of movement, for strengthening a muscle or for facilitating voluntary motor function. Functional Electrical Stimulation (FES) or Functional Neuromuscular Stimulation (FNS) attempts to restore neuromuscular function by applying electrical pulses to neural pathways or to muscles. FES involves depolarizing the nerve or muscle by applying electric current, which causes the ion current within the tissue to depolarize the nerve or muscle to a threshold at which contraction occurs. Different types of electrical pulses or waveforms such as monophase or biphase pulses may be applied. In the case of implanted electrodes, charge-balance pulses are used to avoid a non-zero net charge and electrolysis in the tissue.

Attempts have therefore been made during the last four decades to replace the above-mentioned catheters and surgical procedures with electrical stimulation. Various possible sites for electrical stimulation have been tried, including the spinal cord, spinal sacral nerves, peripheral pelvic nerves and the bladder muscle itself. However, direct muscle stimulation presented several disadvantages including a high energy requirement, high mechanical stress to the electrodes of the muscle area in contact with the electrode and the high number of electrodes required to achieve a uniform contraction. Sacral root stimulation was able to achieve controlled bladder voiding. However, the A-alpha fibers which innervate the external urethral sphincter have a lower stimulation threshold than the A-delta fibers, which innervate the detrusor muscle. Consequently, a higher current is required to stimulate the detrusor muscle and contract the bladder, which simultaneously stimulates and contracts the external urethral sphincter, causing dyssynergia. Ventral sacral root stimulation did not result in a satisfactory bladder voiding pattern owing to the increased urethral resistance associated with high bladder pressure. Sacral root stimulation was refined to reduce contraction of the external urethral sphincter during neurostimulation. Post-stimulus voiding is based on differential relaxation times between detrusor muscle and external urethral sphincter. However, the induced voiding is intermittent instead of continuous with a high voiding pressure that jeopardizes the upper urinary tract. Moreover, post-stimulus voiding is the result of dyssynergia, which requires overcoming urethral resistance by pudendal neurectomy or rhizotomy, which interfere with the anal and sexual functions of the patient.

U.S. Pat. No. 4,771,779 issued to Tanagho et al. on Sep. 20, 1988 discloses a system for controlling bladder evacuation and continence including first and second implanted stimulation systems having electrodes respectively positioned on nerves controlling the external urethral sphincter and the bladder muscle, and an electronic control system which operates to stimulate the external urethral sphincter by the first stimulation system. To void the bladder, a switch is turned on, causing the electronic control system to discontinue the external urethral sphincter stimulation and, after a predetermined delay, to stimulate the bladder muscle through the second stimulation system. After a predetermined time, the bladder stimulation is automatically stopped. After another predetermined delay, the electronic control system resumes the sphincter stimulation through the first stimulation system.

Other methods have been proposed to fatigue the external urethral sphincter by using high frequency current. Selective blocks are based on the difference in the excitation or blocking thresholds of the A-delta and A-alpha fibers. Collision block of the pudendal nerve and anodal block through sacral root stimulation and high-frequency block of the pudendal nerve were reported, in an attempt to achieve selective neurostimulation.

Selective stimulation was proposed to minimize dyssynergia and avoid neurectomy or rhizotomy. Selective stimulation involves the use of a bipolar electrode delivering two different forms of electric stimuli to reach the stimulation threshold of the somatic fibers activating the external urethral sphincter with a high-frequency and low-amplitude signal to block the somatic fibers activity and inhibit the contraction thereof while remaining under the threshold of the autonomic fibers reaching the detrusor muscle. The low-frequency and high-amplitude stimuli activate bladder contraction through the autonomic fibers.

The selective stimulation system is composed of an internal stimulator implanted in the patient and operated with an external hand-held controller. The implant contains a signal generator of a low-frequency and high-amplitude waveform; which stimulates the detrusor muscle, and a high-frequency and low-amplitude waveform, which inhibits contraction of the external urethral sphincter. The two waveforms are joined into a single signal. The generator is connected to a bipolar cuff electrode which is connected to the S2 sacral nerve. The electrode is connected to the internal stimulator which contains a coil. The external controller also contains a coil which establishes a radiofrequency electromagnetic coupling with the coil of the internal stimulator when in proximity thereof, for supplying power thereto. The controller is manually activated by a switch. When the controller is activated and the signal is generated, the high-frequency waveform inhibits the somatic innervating of the external urethral sphincter while leaving the detrusor muscle free to be stimulated by the low frequency waveform and the bladder contraction will achieve voiding.

Although bladder voiding in SCI patients may now be controlled with FES, the problem of bladder atonicity and detrusor muscle hyperreflexia caused by the lack of cerebral inhibition and signal interruption between the bladder and the cerebral cortex through the spinal cord remains.

SUMMARY OF THE INVENTION

An aim of the present invention is to improve rehabilitation of the detrusor muscle, correct bladder atonicity and detrusor muscle hyperreflexia. This is achieved by delivering a low amplitude, low frequency current through an implantable electronic stimulator. The low amplitude, low frequency signal, referred to herein as a tonicity signal, has the effect of gently stimulating the external sphincter muscle to obtain a desired effect of reducing detrusor muscle hyperreflexia.

In accordance with the present invention, there is provided an electronic stimulator implant for improving bladder voiding and preventing bladder hyperreflexia in a patient. The electronic implantable stimulator comprises a tonicity signal generator generating a tonicity signal for preventing bladder hyperreflexia, a self-contained power supply connected to the tonicity signal generator for powering the tonicity signal generator, a voiding signal generator connected to the tonicity signal generator generating a voiding signal for voiding the bladder, a power-receiving circuit connected to the voiding signal generator which includes a receiver coil for powering the voiding signal generator, and an output to an electrode having a first end for connecting to the implant and a second end for connecting to a sacral nerve, whereby when the voiding signal generator is activated, the voiding signal is generated, activating detrusor muscle contraction, thereby activating said bladder voiding.

The tonicity signal provides a basal stimulation required for maintaining the bladder tonicity by modulating the afferent activity of the pelvic floor muscle, and avoid further deterioration due to absence of normal stimulation from the cerebral cortex. The tonicity signal maintains a low-frequency stimulation of the external urethral sphincter, allowing for a better continence and increasing the bladder capacity. For example, the tonicity signal may have a range of frequency from 15 Hz to 40 Hz and a range of amplitude from 500 µA to about 1000 µA. Stimulation of the bladder by the tonicity signal may be constant and may be interrupted during the bladder voiding. The tonicity signal may alternatively be intermittent. In such case, the tonicity signal may be generated at an interval of time, such as with a duty cycle from about 20% to about 80% of a period of about 1 second to about 30 seconds. For example, the tonicity signal may be generated for about 5 seconds at an interval of time of about 15 seconds.

The power supply of the tonicity signal generator may be incorporated in the implant in the form of a battery, such as of the encapsulated type. The tonicity signal generator may be activated through an external controller which may be manually activated by the patient. The external controller may generate a command signal for commanding the tonicity signal generator, and the electronic stimulator implant may further comprise a command interpreter for transmitting the command signal to the tonicity signal generator. The activation of the tonicity signal generator may be controlled by a command received by the power and data receiving circuit.

The voiding signal may activate detrusor muscle contraction without activating external urethral sphincter contraction, and bladder voiding may be achieved without dyssynergia. This may be achieved with a dual waveform of a high-frequency and low-amplitude signal, which inhibits contraction of the external urethral sphincter without contracting the detrusor muscle, and a low-frequency and high-amplitude signal, which activate detrusor muscle contraction without activating contraction of the external urethral sphincter because the high-frequency signal inhibits this contraction.

The tonicity and voiding signal generators may be connected through a selector, for selecting between the tonicity and voiding signals.

In accordance with the present invention, there is also provided a method for generating a bladder tonicity signal and a bladder voiding signal in an implant. The method comprises providing a tonicity signal generator generating a tonicity signal for preventing bladder hyperreflexia and connecting a self-contained power supply to the tonicity signal generator for powering the tonicity signal generator, and providing a voiding signal generator generating a voiding signal for activating bladder voiding and connecting a power-receiving circuit to the voiding signal generator, the power-receiving circuit including a transducer, for powering the voiding signal generator.

In accordance with the present invention, there is further provided a method for improving bladder voiding and preventing hyperreflexia in a patient. The method comprises implanting such an electronic stimulator implant in a subcutaneous pouch of the patient, implanting an electrode in a subcutaneous space of the patient, connecting a first end of the electrode to the implant, and connecting a second end of the electrode to a sacral nerve, thereby transmitting the tonicity signal to the sacral nerve, and manually activating an external controller of the electronic stimulator implant when in proximity thereof, thereby activating the voiding signal generator and transmitting the voding signal to the sacral nerve upon command.

The electronic stimulator implant of the present invention may be used in patients having a dysfunctional bladder, such as spinal cord injured (SCI) patients, or in patients presenting a urinary retention of unknown etiology, and more particularly in patients using an implantable FES system.

An object of the present invention is to provide a mechanism to confirm that the implant is operating properly. According to this aspect of the invention, the implant measures an electrode-tissue contact impedance value. The results of measurement and monitoring are communicated from the implant to inform the patient or health-care provider about the proper operation or malfunction of the implant. This communication may take place by modulation of an inductive powering signal. The implant may also carry out its measurement and monitoring of the electrode-tissue impedance over an extended period of time, as for example by intermittently interrupting supply of a tonicity signal and supplying an active test signal or measuring a tissue potential, and record the results of such monitoring. The compiled results of the monitoring can then be communicated to the patient or health-care provider.

According to this object of the invention, there is provided an electronic stimulator implant comprising a stimulator signal generator, an electrode connected to tissue, e.g. a nerve or surrounding tissue, and an electrode-tissue contact impedance measurement circuit. The implant further comprises either a feedback communications system for communicating a status of the electrode-tissue contact impedance to an external controller, or circuitry for adjusting the stimulator signal generator to maintain a predetermined level of charge injection in the tissue in response to the impedance. Preferably, the electrode is a bipolar cuff electrode, and when the impedance is found to increase, a greater amount of current is fed to the electrode. It will be appreciated that such electrode-tissue impedance monitoring can be applied to various implants other than urinary implants, such as colon or brain implants.

BRIEF DESCRIPTION OF THE DRAWINGS

Having thus generally described the nature of the invention, reference will now be made to the accompanying drawings, showing by way of illustration a preferred embodiment thereof, in which like numerals refer to like components and in which.

DETAILED DESCRIPTION OF THE INVENTION

Figure 1:
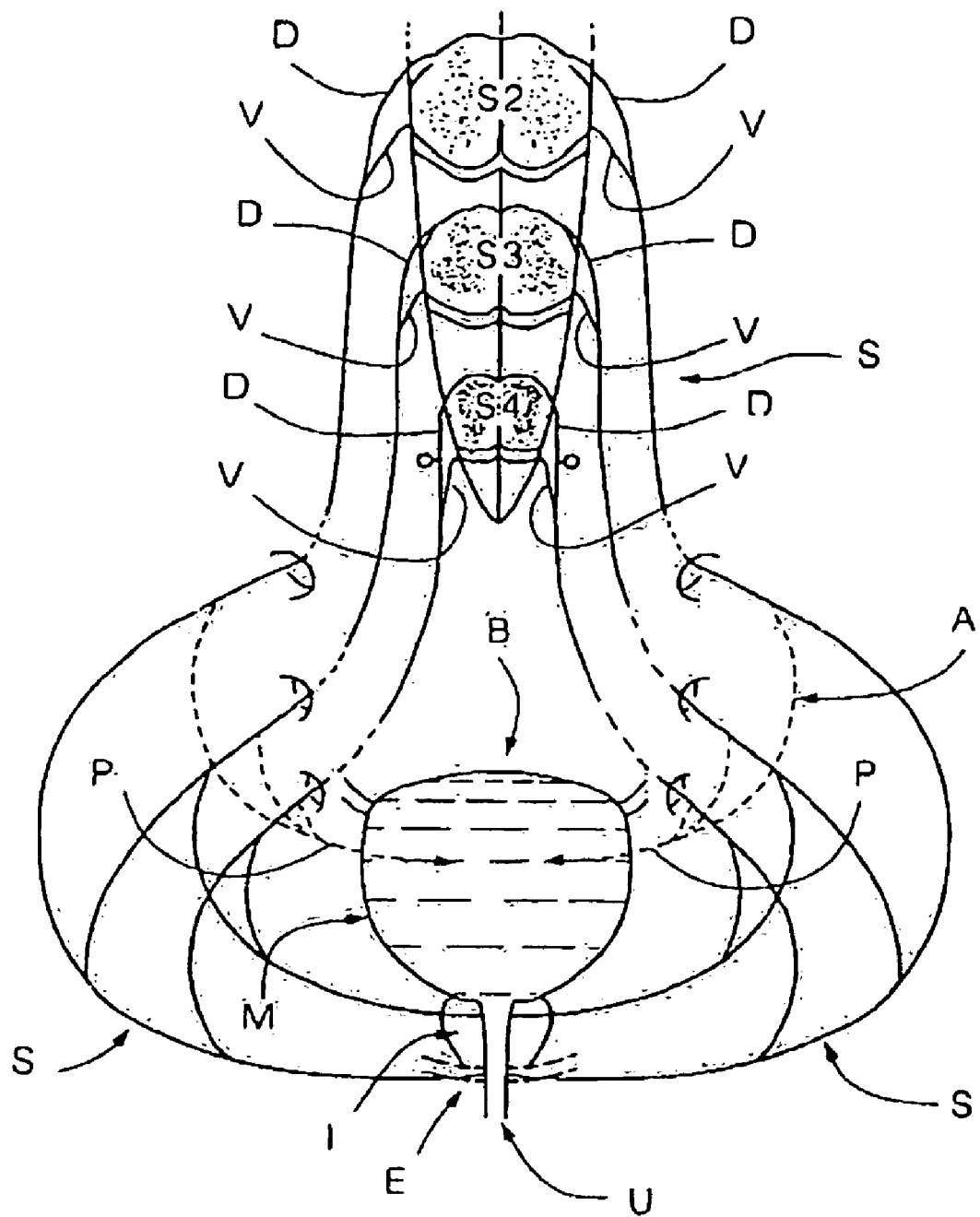
FIG. 1 schematically illustrates the nervous system for controlling bladder voiding and related functions.

In accordance with the present invention, there is provided an electronic stimulator implant for improving bladder voiding and preventing bladder hyperreflexia in a patient and which may eliminate detrusor-sphincter dyssynergia and hyperreflexia and maintain tonicity of the pelvic floor muscle of the bladder as shown in FIG. 1.

Figure 2:
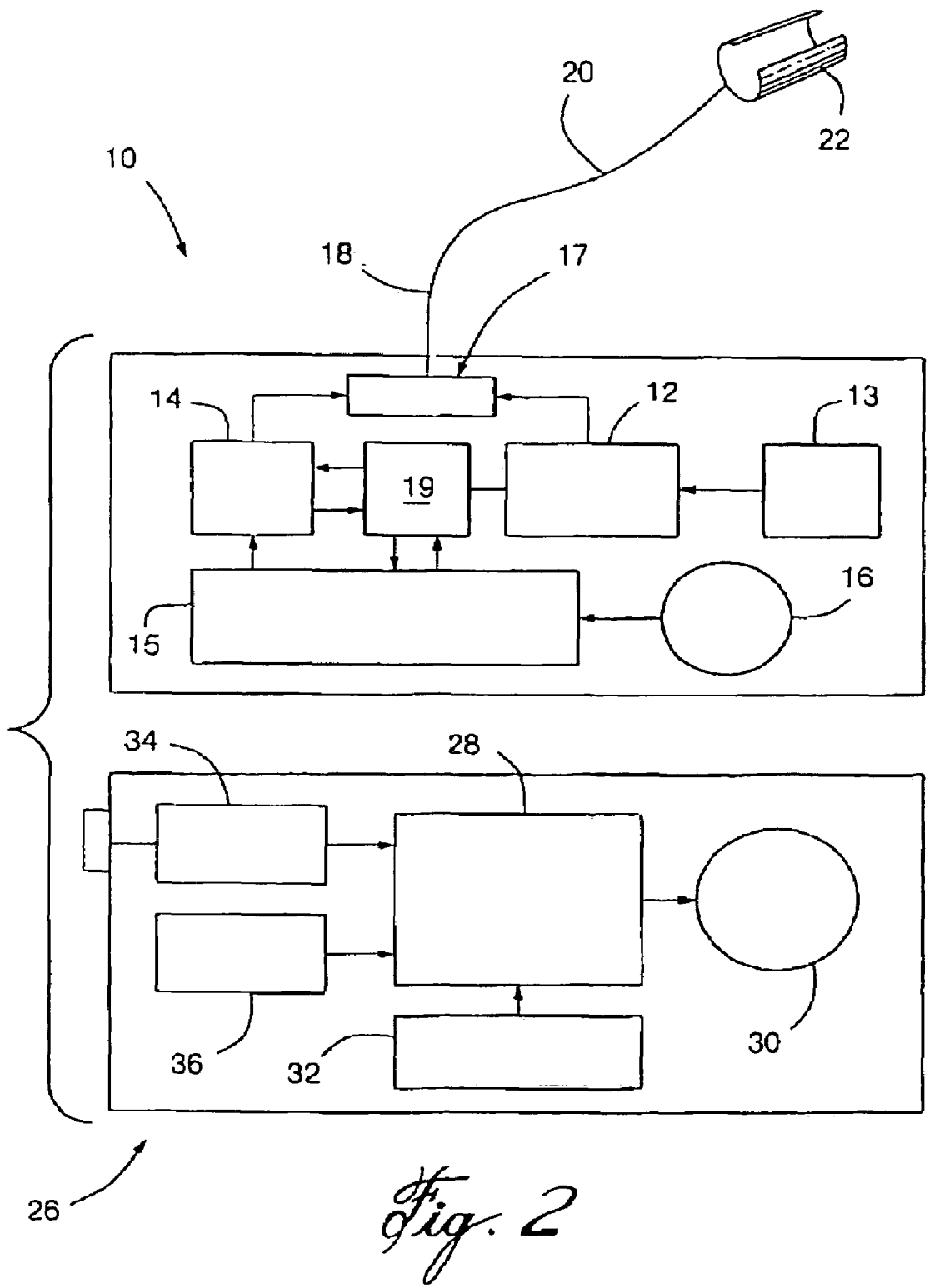
FIG. 2 schematically illustrates an electronic stimulator implant in accordance with the present invention, including an electronic stimulator for maintaining bladder stability and a stimuli generator for a selective stimulation of the bladder.
Figure 3:
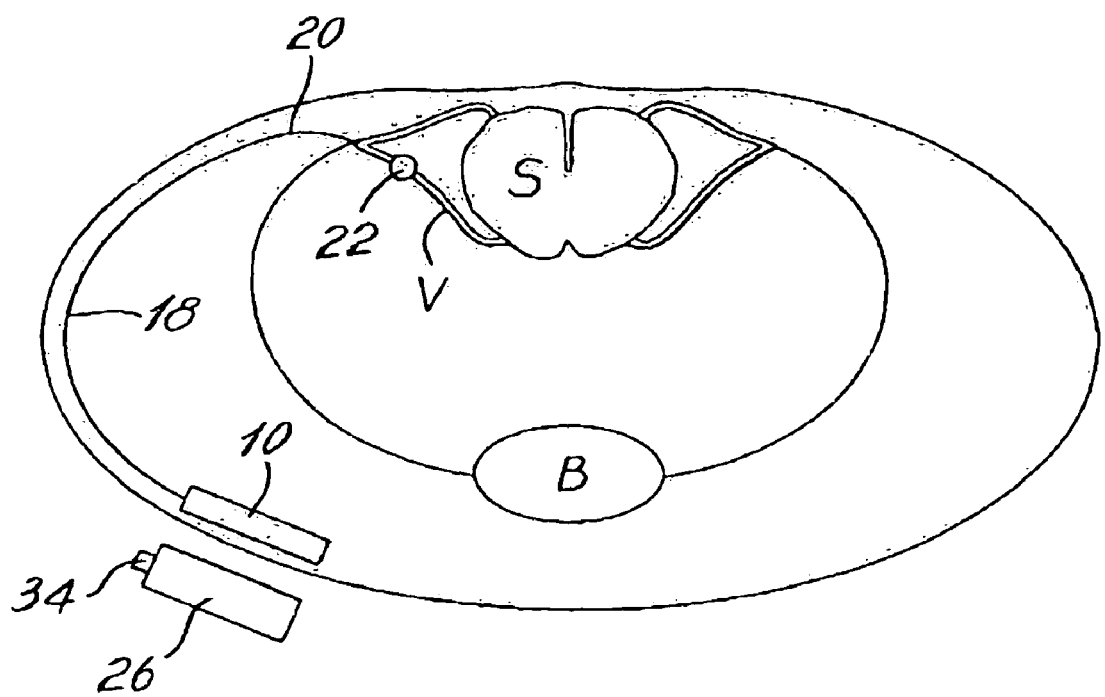
FIG. 3 illustrates in a cross-sectional view the electronic stimulator implant illustrated in FIG. 2, shown implanted in a patient and integrated in a functional electrical stimulation system.

FIG. 2 illustrates an electronic stimulator implant for maintaining the bladder in accordance with the present invention, which is identified by reference numeral 10. A tonicity signal generator 12 is contained in the electronic stimulator implant 10. The tonicity signal generator 12 generates a tonicity signal which prevents bladder hyperreflexia by maintaining the tonicity of the pelvic floor muscle of the bladder, its effect on the reflex arc slows down contractions of the detrusor muscle which normally occurs in absence of feedback stimulation from the brain, thereby preventing hyperreflexia. A battery 13 is connected to the tonicity signal generator 12, for providing power thereto.

A voiding signal generator 14 is also contained in the electronic stimulator implant 10. The voiding signal generator 14 generates a functional electrical stimulation (FES) signal to activate the bladder voiding process upon command. The voiding signal generator 14 generates a single signal which combines a first waveform of a low frequency and high amplitude, which activates contraction of the detrusor muscle, and a second waveform of a high frequency and low amplitude, which inhibits contraction of the external urethral sphincter of the bladder, thereby achieving bladder voiding without dyssynergia.

An AC-DC voltage converter and regulator 15 is connected to the voiding signal generator 14, for providing DC power thereto. A receiving coil 16 is connected to the power converter 15. The coil 16 receives a power AC signal from coil 30 by inductance coupling. AC-DC voltage converter and regulator 15 rectifies and regulates a voltage signal. The command signal is modulated over the AC power signal by generator 28. A command signal and feedback communications circuit 19 is connected to the coil 16 via regulator 15. A modulated information signal generated by circuit 28 is detected, demodulated and decoded by circuit 19. Circuit 19 thus transmits a command signal to the tonicity signal generator 12 as will be explained hereinafter. While the voiding signal generator 14 can operate automatically when power is supplied by circuit 15, preferably, circuit 19 supplies a command signal to turn on and off the voiding signal.

Likewise, circuit 19 is able to vary an impedance of coil 16 so that the variation of impedance can be detected by circuit 28 in order to communicate feedback data from the implant to the device 26.

The electrode-tissue contact impedance can be monitored either by generator 14 or by generator 12. For example, the current flow to the electrode can be measured during the supply of the voiding signal, and this measured current value can be compared with stored values. The status of the contact impedance can be communicated to the device 26 and an indicator (not shown) connected to circuit 28 can indicate the status of the electrode-tissue contact.

Preferably, the impedance is measured using a voltage to frequency converter which converts the voltage at the electrode to a frequency. The frequency signal is then sampled over a time window and converted using a frequency counter circuit which outputs an 8-bit word corresponding to the frequency, i.e. the measured voltage at the electrode. The measured voltage is related to the electrode-nerve impedance. The impedance to frequency conversion and the frequency to 8-bit word conversion circuitry is also described in "implantable measurement technique dedicated to the monitoring of electrode-nerve contact in bladder stimulators", Med. Biol. Eng. Comput., 2000, 38, 465-468, the content of which is hereby incorporated by reference. The impedance measurement is used firstly to adjust the amplitude of the signal generators 12,14 to ensure that the injected charge into the nerve remains constant over time for the tonicity and voiding signals. The impedance value (i.e. the 8-bit word) is also communicated to the device 26 as mentioned above, using for example frequency modulation in the signal between the device 26 and the implant.

Outputs of tonicity and voiding signal generators 12,14 are connected through a selector 17. The selective 17 normally allows the signal from generator 12 to pass through. Upon command, the selector 17 is turned off to discontinue the tonicity signal when generator 14 operates. This is preferred, although not essential.

A bipolar electrode has a first end 18 connected to the selector 17 and a second end 20 for connecting to a sacral nerve, such as the S2 sacral segment. A cuff 22 is disposed at the second end 20, for attachment to the sacral nerve. The cuff 22 is preferably made of a shape memory alloy (SMA) and isolated by silastic, which is cooled to open before and during placement on the nerve. The cuff 22 then warms up to body temperature and elastically grasps the nerve firmly with the exact desired pressure. The electrode comprises two Teflon™ coated stainless steel wires connected to platinum contacts having a 25 µm thickness. The contacts are separated in the axial direction of the nerve by about 1 to 2 mm, and molded in an elastomeric envelope made of silastic and provide the electrical connection to the nerve. Various methods of wrapping the contacts around the nerve can be used, although the SMA cuff electrode is preferred.

The electronic stimulator implant 10 is activated by an external controller 26. The external controller 26 contains a power generator 28. A transmitting coil 30 is mounted to the power generator 28. A batter 32 is connected to the power generator 28, for providing power thereto. A switch 34 is connected to the power generator 28, to allow the patient to manually activate the power generator 28. Upon activation of the switch 34, the power generator 28 provides power to the voiding signal generator 14 using electromagnetic coupling between the transmitting coil 30 and the receiving coil 16 of the implant 10. The transmitting coil 30 establishes an electromagnetic AC coupling with the receiving coil 16 of the implant 10 when in proximity thereof, for supplying power thereto and for transmitting a control signal to the implant 10. However other coupling techniques may be used in addition to radio-frequency magnetic inductance coupling, such as an optical receiver and infrared. A versatile version of the controller includes a keyboard, display, and allows all stimuli parameters to be programmed. The external controller used for programming stimuli parameters is thus preferably a more sophisticated controller than unit 26, the latter being used by the patient.

A processing unit 36 is contained in the external controller 26 and connected to the power generator 28. The control signal from the power generator 28 sets the needed parameters, such as frequency and/or amplitude of the voiding signal, and determines a continuous or intermittent mode for the tonicity signal. The control signal generated by the processing unit 36 of the external controller 26 is received by the voiding signal generator 14 (via circuit 19).

Figure 4:
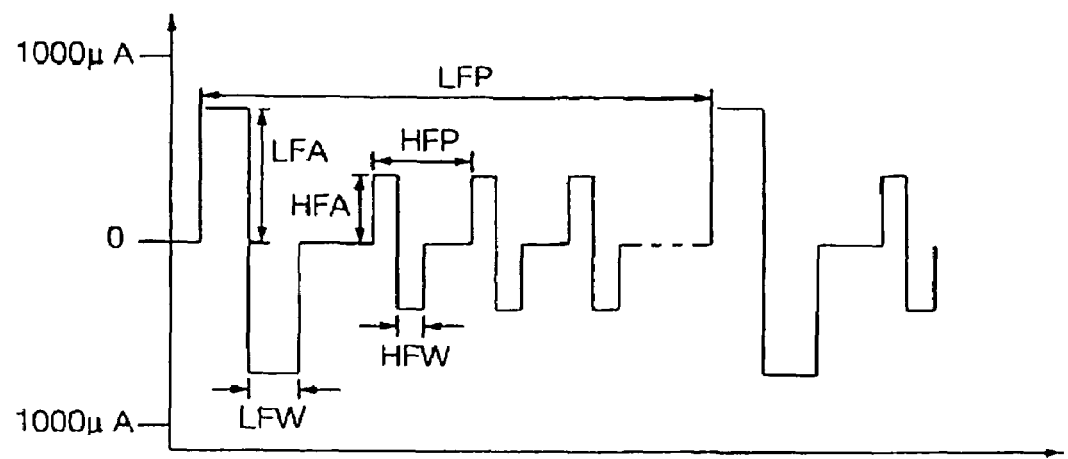
FIG. 4 illustrates the waveform generated by the voiding signal generator of the electronic stimulator illustrated in FIG. 2 (*a*) compared to the waveform generated by the tonicity signal generator (FIG. 2 (*b*)).
Figure 4:
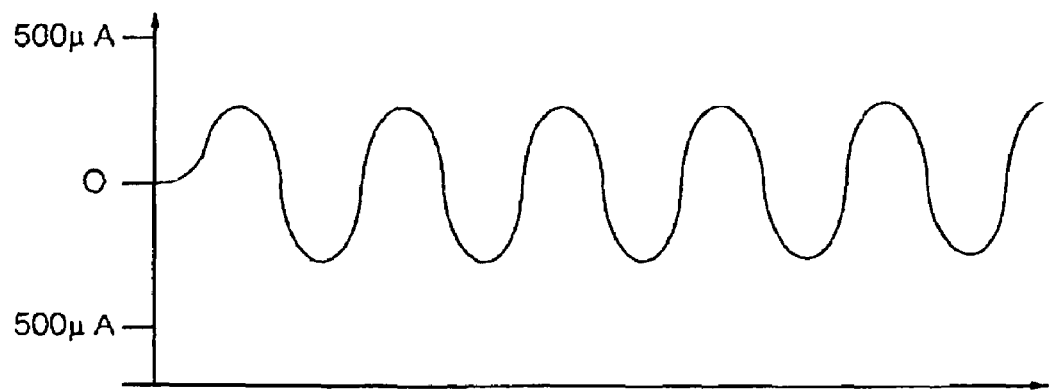

FIG. 4 illustrates the waveforms generated by the tonicity signal generator 12 (below) compared to the waveform generated by the voiding signal generator 14 (above). In the waveform generated by the voiding signal generator 14, LFA corresponds to the low frequency amplitude. LFW to the low frequency pulse width, LFP to the low frequency period, HFA to the high frequency amplitude, HFW to the high frequency pulse width and HFP to the high frequency period. The high frequency signal amplitude may vary from 0 to 3 mA and the pulse width of the high frequency signal from 10 to 900 μsec.

The amplitude of the tonicity signal is about 25% to 50% of the amplitude of the voiding signal. The lower power level required makes it practical to use a self-contained power source such as battery 13 for powering the first signal generator 12.

Through a surgical procedure, the implant 10 is inserted in a subcutaneous pouch in proximity of the surface of the skin of a patient, while an electrode is superficially inserted in the subcutaneous space. The second end of the electrode 20 thereof is connected to the sacral root via the cuff 22. The implant 10 generates continually or intermittently the tonicity signal, to maintain a basic stimulation of the external urethral sphincter and the pelvic floor muscle. The tonicty signal requires a minimum of energy from the battery 13 in the implant 10.

To activate bladder voiding, the patient holds the external controller 26 and puts it close to the skin area of the body covering the implant 10. The patient then activates the manual switch 34 of the external controller 26. A control signal is generated by the processing unit 36 of the external controller 26, which is transmitted by radiofrequency electromagnetic coupling from the transmitting coil 30 to the receiving coil 16 in the implant 10. Upon receiving the control signal, the voiding signal generator generates a combined FES waveform as described above, which is transmitted through the electrode 22 to the sacral nerve. The high-frequency waveform of the voiding signal inhibits the somatic fibers innervating of the external urethral sphincter of the bladder while leaving the detrusor muscle thereof free to be stimulated by the low-frequency waveform, thereby voiding the bladder.

The voiding signal generator 14 can be provided by an FPGA. The generator can be provided by a low-power consumption microcontroller, such as the Microchip™ PIC based on a surface mount component, and both generator circuits can be provided by an optimized dedicated full custom Integrated circuit (IC) device. Preferably, a single Application Specific Integrated Circuit (ASIC) is used for providing the two signal generator functions with minimal power consumption.

While the invention has been described with particular reference to the illustrated embodiment, it will be understood that numerous modifications thereto will appear to those skilled in the art. Accordingly, the above description and accompanying drawings should be taken as illustrative of the invention and not in a limiting sense.

The invention claimed is:

1. An electronic stimulator implant comprising:
   a stimulator signal generator;
   an electrode adapted to be connected to tissue; and
   an electrode-tissue contact impedance measurement circuit which converts a voltage at said electrode to a frequency and converts said frequency into a digital value signal;
   wherein said implant further comprises at least one of:
      a feedback communications system for communicating a status of said electrode-tissue contact impedance to an external controller; and
      circuitry for adjusting said stimulator signal generator to maintain a predetermined level of charge injection in said tissue in response to said impedance.

2. The implant according to claim 1, wherein said feedback communication system communicates directly said digital value signal to said external controller.

3. The implant according to claim 2 wherein said electrode is a bipolar cuff electrode, and when the impedance is found to increase, a greater amount of current is fed to the electrode.

4. The implant according to claim 1, wherein said electrode is a bipolar cuff electrode, and when the impedance is found to increase, a greater amount of current is fed to the electrode.

* * * * *